United States Patent [19]

Stein

[11] Patent Number: 4,844,066
[45] Date of Patent: Jul. 4, 1989

[54] SURGICAL CLIP
[75] Inventor: Jeffrey A. Stein, Milford, Conn.
[73] Assignee: Richard-Allan Medical Industries, Inc., Richland, Mich.
[21] Appl. No.: 35,075
[22] Filed: Apr. 6, 1987
[51] Int. Cl.[4] ............................................. A61B 17/12
[52] U.S. Cl. .................................. 128/325; 128/346; 24/20 CW; 24/115 A
[58] Field of Search ............... 128/326, 325, 346, 337; 24/30.5 W, 20 CW, 115 A, 703; 227/DIG. 1

[56] References Cited

U.S. PATENT DOCUMENTS

| | | | |
|---|---|---|---|
| 733,723 | 7/1903 | Lukens | 128/337 |
| 3,326,216 | 6/1967 | Wood | 128/325 |
| 3,344,649 | 10/1967 | Wood . | |
| 3,827,438 | 8/1974 | Kees, Jr. . | |
| 3,867,944 | 2/1975 | Samuels | 128/325 |
| 4,344,531 | 8/1982 | Giersch . | |
| 4,505,274 | 3/1985 | Speelman | 128/337 |
| 4,509,518 | 4/1985 | McGarry et al. . | |
| 4,616,651 | 10/1986 | Golden . | |
| 4,624,254 | 11/1986 | McGarry et al. | 128/325 |

Primary Examiner—Michael H. Thaler
Attorney, Agent, or Firm—Neuman, Williams, Anderson & Olson

[57] ABSTRACT

The present invention relates to a surgical clip for occluding the flow of blood through a blood vessel, artery or vein. The clip formed with longitudinal and transverse or lateral notches to prevent both longitudinal and lateral slippage of the clip with respect to the vessel. The clip is also provided with coined front legs to assist in deformation about a vessel and to further provide a self aligning feature when the clips are arranged in an abutting, forward facing row. The apparatus of the present invention forms the foregoing described clip and does so in a symmetrical way to provide a clip with a uniform stock length.

7 Claims, 2 Drawing Sheets

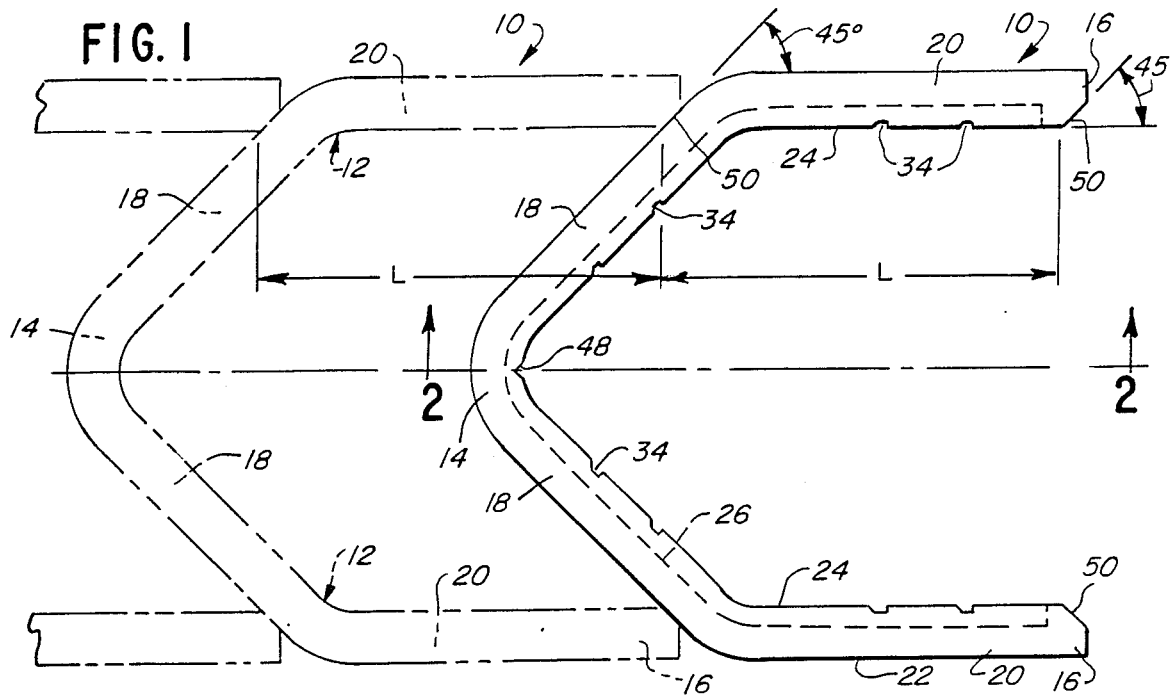
FIG. 1
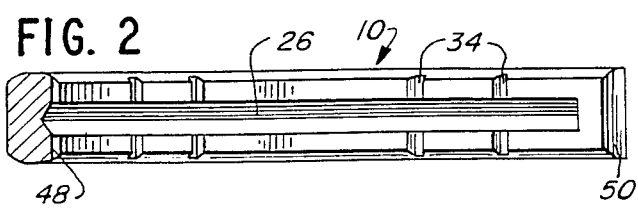
FIG. 2
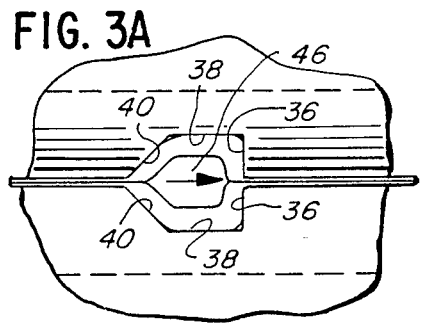
FIG. 3A
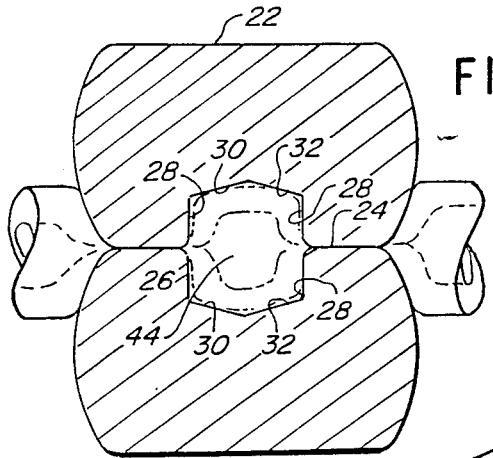
FIG. 7
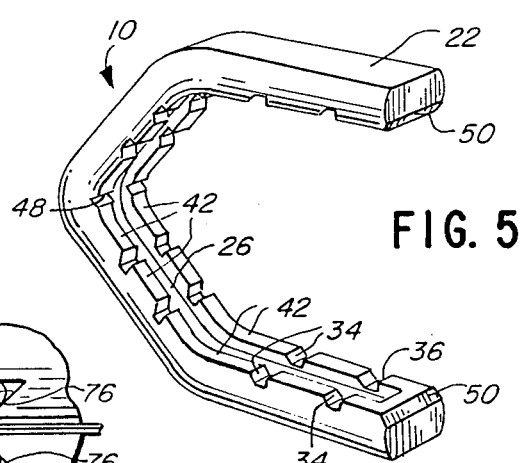
FIG. 5
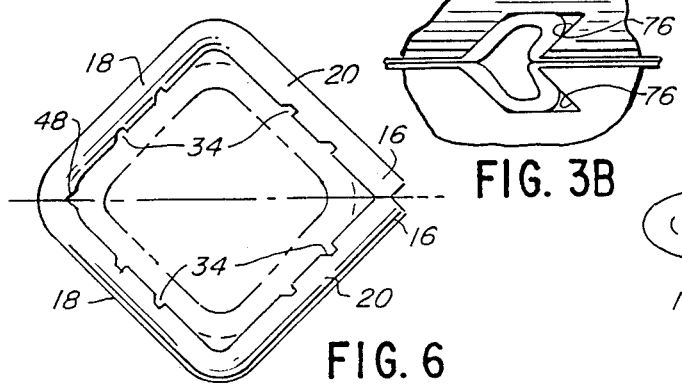
FIG. 3B
FIG. 6
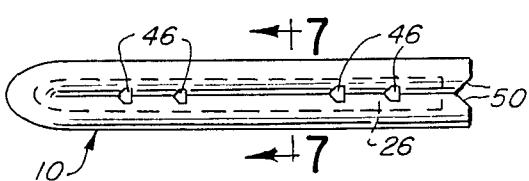
FIG. 4

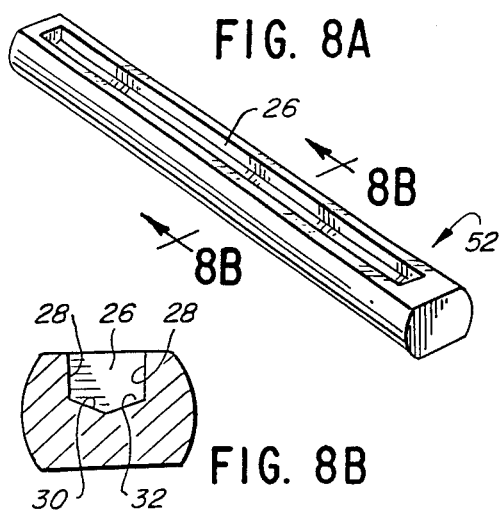
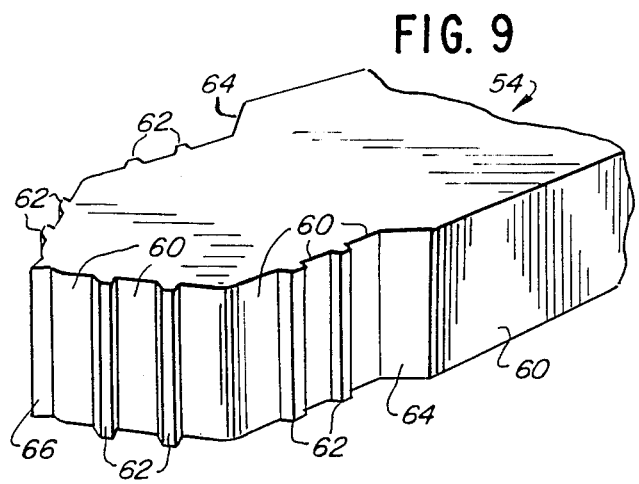
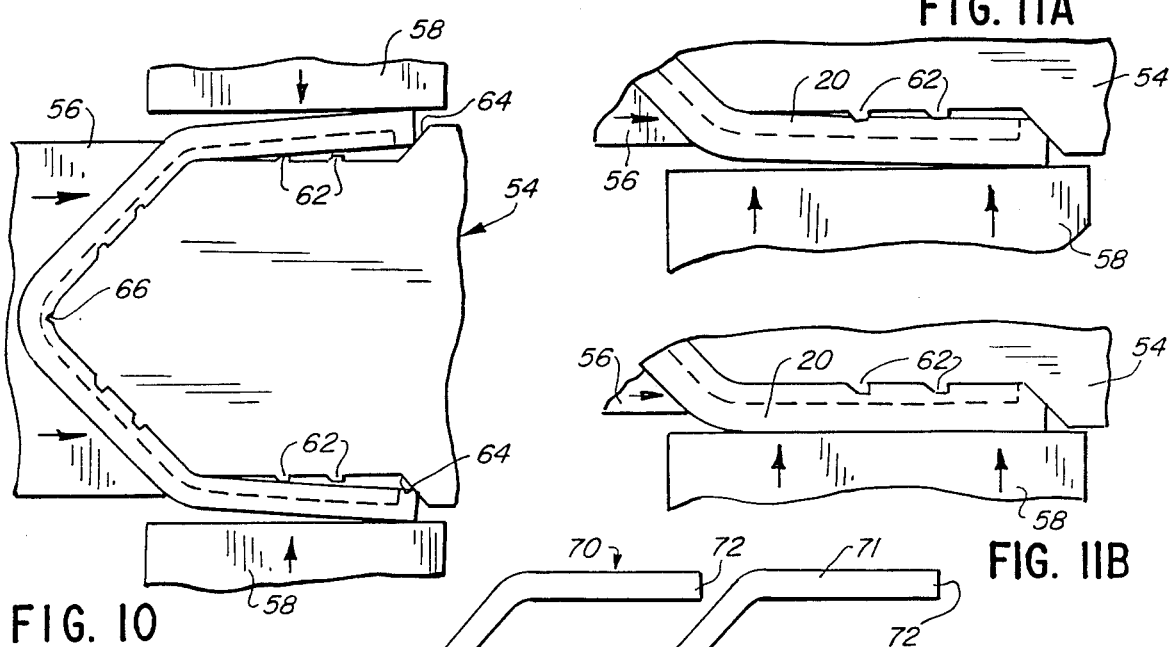
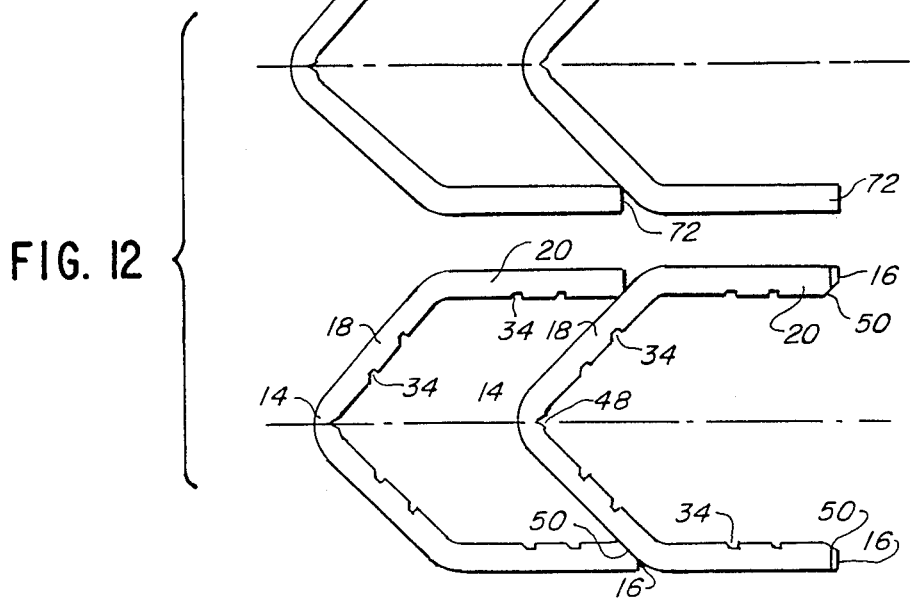

SURGICAL CLIP

BACKGROUND OF THE INVENTION

Field of the Invention

The present invention relates to a surgical clip and the apparatus for manufacturing that clip. More particularly, the present invention concerns a novel surgical clip design to be applied to a vein, artery or other blood vessel during surgery to constrict or close the vessel at a specific location so that the vessel may be severed or cut without subsequent loss of blood.

Ligation or occlusion of veins, arteries or blood vessels has been a necessary part of surgical procedures for many years. Initially, surgeons used thread or suture material to tie a blood vessel prior to severing the vessel. This procedure required both skill and time on the part of the surgeon to properly close the vessel. In many instances, assistance of a nurse or attending surgeon was necessary and typically, a severed blood vessel would require closure on both sides of a severance site before actual cutting could take place. The advent of surgical clips and clip appliers has greatly enhanced this procedure.

Many factors are critical to the design of a surgical clip. Among these, it is important that the clip not slip or become dislodged from a blood vessel after the blood vessel is severed. In that instance, blood will immediately begin flowing into the surgery site through the unclamped vessel requiring the operation be delayed while the critical vessel is located and reclamped. Depending on the type and location of the surgery, locating the vessel may be difficult and the time delay could cause medical complications to the patient.

Similarly, a clip must be designed to fully and completely close about a vein, artery or blood vessel and completely stop the flow of blood through these pathways. A clip which does not completely occlude the flow of blood is useless for its intended function. In addition, if the clip is of such a size or is designed in such a manner that during deformation about a vessel a portion of the vessel is allowed to extend beyond the tips of the clip legs, the clip will obviously not completely restrict the flow of blood and similar serious problems could arise. Consequently, besides insuring that the vessel is completely trapped within the clip, the clip must be designed such that when it is completely formed about a vessel the flow of blood through the vessel is completely precluded.

Generally, surgical clips are U-shaped or V-shaped members having two legs joined at an apex or crown portion and spaced apart at the opposite end. Typically, the inside surface of the clip legs are deformed in some manner, such as having varying types of holes, slots or grooves, in an attempt to improve the occluding functions of the clip after the clip has been deformed about a blood vessel. Instead of achieving this desired end result, many prior art designs actually promote the lateral slippage or opening of a clip after it has been applied about a vessel.

Within these design considerations, care must be taken to avoid employing sharp edges of any kind which might cause the vessel to be cut or severed by the clip during formation. The design of many prior art clips promote inconsistent deformation which in combination with the shape of the clip can cause the clip to sever or damage the blood vessel thereby requiring additional clips be applied to restrict the flow of blood and, subsequently, the damaged vessel be repaired.

Not only must clips be made uniformly so that each and every clip will consistently deform in the same manner, but the nature of clip appliers for applying and deforming clips has progressed and added new demands to the design of a surgical clip. Originally, clip appliers were scissors or pliers type instruments in which a single individual clip was manually inserted between the jaws of the instrument and then subsequently deformed about a blood vessel. As a result, the exact design of the clip with respect to its fit within the clip aplier was not critical. Clip appliers are now available which house clip cartridges or magazines containing 35 or more individual clips. Consequently, not only must each of these individual clips perform in exactly the same way but the design of the clip now must also account for storage and advancement of the clip in the many different clip cartridges and magazines employed in multiple count clip appliers.

For example, in some multiple count clip apliers the clips are abuttingly arranged in a single forward facing row wherein an advancing force is applied to the last clip in the row and each clip pushes or advances the clip in front of it. Under these conditions the design of the clips must act to maintain the row of clips in alignment. However, if the legs of a clip are different in length, as can easily happen under conventional manufacturing methods, the clip will not properly align with the next forwardmost clip. This will ultimately cause the entire row to become unaligned as the clips are pushed forward in the clip magazine. In addition, if the tip of each leg is not shaped to receive and engage the crown of a clip, the row of clips similarly could become unaligned. This is the case with conventional clips where the crown of the clip is angled with respect the flat forward tips of the legs.

These problems are resolved by providing a clip with a uniform clip stack length and a modified leg tip design. Clip stack length is defined as the distance between the chamfered clip leg tips on abutting clips measured between the point at which the beveled surface joins the inside surface of the clip. By maintaining a uniform clip stack length for each clip and by modifying the tip of the clip leg to cooperate with the shape of the clip crown, the row of clips will become self-aligning and advancement of the row of clips will be enhanced. Moreover, the availability of clips with a uniform stack length will allow clip applier manufacturers to forget the problems of clip feed inherent with the use of clips having varying clip lengths. The apparatus for manufacturing the clip of the present invention insures the production of clips with a uniform stack length and a leg tip configuration adapted to cooperate with the crown or apex of the clip.

In other types of clip magazines the design of the clip is not a factor in the feed or advancement of the clips. These types of magazines or cartridges employ a complex arrangement of teeth or similar devices which separately hold and advance the clips without any contact between clips or vertically stack the clips one on top of another. The clip of the present invention will function in these cartridges as well.

The present clip is designed with a longitudinal center channel or groove and a series of transverse notches which, when the clip is deformed, cooperate to create a clip which prevents the flow of blood and further prevents lateral and longitudinal slippage on the vessel. In addition, the apparatus for manufacturing the clip insures reliable and uniform deformation of each and every clip in such a manner that the clip will not damage or sever a blood vessel and will produce a clip with a uniform stack length which can be used in almost any cartridge or magazine of a multiple clip applier employing standard surgical clips.

OBJECTS OF THE INVENTION

It is the general object of this invention to provide an improved surgical clip.

It is another object of this invention to provide a surgical clip having a design which prevents longitudinal or lateral slippage of the clip after it is deformed about a blood vessel.

It is another object of this invention to provide a clip which will deform in such a manner that the tips of the clip legs will engage first to entrap or encompass the blood vessel within the clip before the clip fully deforms.

It is a further object of this invention to provide an apparatus for manufacturing surgical clips in such a manner that the resulting clips will always symmetrically and uniformly deform about a blood vessel and will not sever or cut the vessel during deformation.

It is still another object of this invention to provide a clip having a plurality of symmetrical notches or grooves which, when the clip is deformed, overlap in an aligned manner to prohibit the flow of blood through a blood vessel about which the clip is deformed and prevent slippage of ;the clip with respect to the vessel.

It is still a further object of the present invention to provide an apparatus for manufacturing clips which create a clip having a consistent uniform stack length so that a plurality of clips can be employed in a clip cartridge or magazine for use in a multiple count clip applicator.

Other objects and advantages of the present invention will become apparent upon reading the following detailed description and appended claims, and upon reference to the accompanying drawings.

IN THE DRAWINGS

For a more complete understanding of this invention, reference should now be made to the embodiment illustrated in greater detail in the accompanying drawings and described below by way of examples of the invention.

FIG. 1 is a top view of a partial row of forward facing clips of the present invention.

FIG. 2 is a cross sectional view of the clip of the present invention taken along line 2—2 of FIG. 1.

FIG. 3A is an enlarged partial side view of a pair of lateral notches formed in opposite legs of the surgical clip of the present invention and in aligned overlying position after the clip has been deformed.

FIG. 3B is an enlarged partial view of an alternative embodiment of the lateral notches formed in the clip legs and in aligned overlying position after the clip has been deformed.

FIG. 4 is a side view of a deformed clip of the present invention showing the lateral notches in aligned overlying position.

FIG. 5 is an elevated perspective view of the clip of the present invention.

FIG. 6 is a side view of the surgical clip of the present invention after partial deformation with the leg tips in registered alignment and completely trapping a blood vessel within the clip.

FIG. 7 is a cross sectional view of a deformed clip taken along line 7—7 of FIG. 4.

FIG. 8A. is an elevated perspective view of the discrete wire segment used to form a clip of the present invention after the longitudinal groove has been formed in the wire.

FIG. 8B is a cross sectional view of the discrete wire segment taken along line 8B—8B of FIG. 8A.

FIG. 9 is an elevated view of the mandrel of the present invention.

FIG. 10 is a top view of the apparatus employed to form the discrete wire segment shown in FIG. 8A into the clip of the present invention.

FIG. 11A is a partial top view of the apparatus shown in FIG. 10 showing further formation of a clip leg.

FIG. 11B is a partial top view of the apparatus shown in FIG. 10 showing complete formation of a clip leg.

FIG. 12 is a comparison between a pair of conventional clips placed in a forward facing abutting relation and a pair of clips of the present invention placed in a forward facing abutting relation.

SUMMARY OF THE INVENTION

The present invention covers an improved surgical clip and the apparatus used for making that clip. A surgical clip is applied to a blood vessel, vein or artery during surgery to occlude the flow of blood while some other surgical procedure is being performed. In that context it is critical that the clip completely occlude the blood flow and not slip off or become dislodged from the vessel once applied. The pattern of longitudinal and lateral grooves or notches formed on the inside surface of the clip legs, prevent the clip of the present invention from slipping off the vessel once it is deformed about the vessel.

The clip of the present invention is further designed so that, upon closure, the blood vessel is completely trapped before the clip is completely deformed. This is accomplished by bringing the clip leg tips together before completely deforming the clip and insures that no portion of the blood vessel extends outside the end of the deformed clip thereby insuring complete occlusion of the blood flow. Additionally, the coined or beveled leg tips provide a flat surface for the initial joining of the legs and act to prevent scissoring of the legs during clip deformation which can cause the vessel to be severed or cut by the clip. Indeed, the design of the leg tips promotes registered alignment of the clip legs.

The clip of the present invention is further designed to be used in any multiple clip applier which employs conventional clips. However, the design of the clip allows a plurality of the clips to be placed in an abutting forward facing row and thereby provide a self aligning and self feeding array of clips. This allows the clip cartridge or magazine to be constructed more simply than present complex clip magazines which employ individual and separate fingers or teeth for engaging and advancing the clips.

The present invention also includes a novel apparatus for forming the surgical clip having the features set forth above.

DETAILED DESCRIPTION OF THE INVENTION

The relationship and use of the various features of this invention will be better understood by the following detailed description. However, the embodiment of the invention described below is by way of example only and applicants do not limit themselves to this embodiment. Furthermore, one should understand that the drawings are not to scale and that the embodiments are illustrated in part by graphic symbols and fragmentary views. In certain instances, details may have been omitted which are not necessary for an understanding of the present invention.

As shown in FIG. 1, the surgical clip 10 of the present invention is defined by a pair of legs 12 joined together at one end by a curved or bight portion 14 to form a crown and spaced at the opposite or distal end 16. More particularly, in the surgical clip of the preferred embodiment, each leg is divided into a first and second portion. The first portions 18 of each leg are disposed at a 45° angle with respect to the center line of the clip and are interconnected to form the crown or apex of the clip. The respective second portions 20 extend from the first portions and are disposed in a spaced, parallel relationship with respect to each other (FIG. 1). As can further be seen from FIGS. 5 and 8, the surgical clip 10 of the present invention is formed from flattened wire to provide the clip with that exterior and interior surfaces 22 and 24, respectively.

As can readily be seen in FIGS. 2 and 5, a clip of the present invention has a longitudinal center groove or channel 26 which extends approximately the entire length of the inside surface 24 of the clip 10. As best seen in FIG. 7, this groove or channel 26 has two spaced vertical side walls 28 and a bottom wall defined by two slanted or beveled sections 30 and 32, respectively. In addition, a plurality of lateral grooves or channels 34 are also formed on the inside surface 24 of the clip and bisect the longitudinal channel 26. These channels have a vertical front wall 36, a horizontal bottom wall 38 and a sloped rear wall 40 (FIG. 3a). As graphically shown in FIG. 5, the result of the longitudinal and lateral channels is to form two spaced parallel rows of shoulders or teeth 42 along the outside edge of the internal surface of the clip.

The longitudinal channels 26 and lateral channels 34 are symmetrically formed with respect to each leg of the clip. As a result, upon deformation of the clip about a vessel, the longitudinal channel 26 is placed in an adjacent, overlying or registered relationship with itself (FIG. 7), and the plurality of lateral channels 34 are similarly placed in adjacent, overlying or registered relation as well (FIG. 3a and FIG. 4). The result is to form longitudinal and lateral cavities, 44 and 46, respectively, having at least one set of vertical walls.

The vertical walls formed by the overlying channels are critical to the ability of the clip to preclude slippage with respect to the vessel. Once deformed about a vessel, external forces applied to the clip may tend to cause the clip to slide either longitudinally or laterally with respect to the vessel. The longitudinal and lateral channels of the present invention are designed to prevent this slippage.

As can be seen in FIG. 7, the vessel about which the clip 10 is applied tends to swell and fill the cavity formed by the longitudinal channel 44. Subsequently, if a force is applied to the clip 10 in an attempt to slide the clip longitudinally with respect to the vessel, the swollen part of the vessel captured within the longitudinal cavity 44 will press against the side walls 28 of the cavity 44. Because the walls 28 are vertical a longitudinal force applied on the clip will be counterbalanced by an opposite force applied by the vessel within the longitudinal cavity 44. As a result, the clip 10 will be prevented from longitudinal movement with respect to the vessel and will not slip off the vessel. However, if the side walls 28 of the longitudinal cavity 44 were slanted toward the exterior edge instead, the reactive force applied by the vessel, when broken into its component forces, would have a component that would tend to open the clip and allow the clip to slide off the vessel.

The lateral cavities 46 formed by the combined lateral channels 34 act in essentially the same manner to prevent lateral slippage of the clip 10 with respect to the blood vessel. As seen in FIG. 3a, the vessel about which the clip is deformed also swells to fill the cavities 46 formed by the overlying lateral channels 34. These lateral cavities 34 have a vertical front wall 36 and, consequently, if the clip is pulled or subjected to some lateral force with respect to the vessel in an effort to remove the clip from the vessel, the front walls 36 of the respective lateral cavities 46 act to preclude the clip from opening and to preclude the clip from being removed from the vessel. If the side 36 walls of the lateral cavity 46 were slanted toward the open end of the clip instead, the vessel would apply a reactive force which would tend to open the clip and allow the clip to slide off the vessel.

As can be best seen in FIG. 1, the clips are further provided with a lateral or transverse notch 48 at the center of the crown or curved portion 14. The lateral notch 48 at the apex of the clip insures that the clip be symmetrically deformed about its center and that during deformation the leg tips 16 are joined first in order to completely trap the vessel before the clip is totally deformed (FIG. 6). The deformation of conventional clips can often lead to a portion of the vessel protruding out the tip of the clips and thereby not totally occluding the flow of blood. A completely deformed clip is shown in FIG. 4.

As can also be seen in FIG. 1, the legs are provided with a chamfered or coined surface 50 along the inside front tip. The coined front edges 50 provide a pair of flat surfaces for the leg tips 16 to join and entrap the vessel and further act to prevent scissoring of the legs during deformation (FIG. 6). Scissoring occurs when the legs 12 do not align or coincide after deformation but, instead, are offset at the tips 16 with respect to each other. Because the surfaces of the present clip are flat rather than rounded the legs of the clips do not slip with respect to each other after tip contact and, therefore, do not scissor or become unaligned. Such an occurrence can cause the clip to cut or even sever the blood vessel thereby requiring further surgical procedures to correct this damage. Scissoring can also prevent the clip from closing completely about the vessel.

In addition to providing a surgical clip 10 with improved occluding characteristics, the design of the present surgical clip allows the clip to be used in many different multiple count or single count clip appliers. However, the present clip 10 is primarily intended to be used in a multiple count clip applier where the clips are abuttingly arranged in a forward facing row with each clip engaging and pushing or advancing the clip in front of it. In an instrument having this type of feed, it is critical that the clips have a uniform stack length so that the clip appliers can be mass produced with a single, uniform unit length of clip advance. By providing a clip with a uniform stack length, the manufacturer of the clip applier can build his instrument without worrying about variations in clip manufacture. In contrast, variation in clip manufacture do not effect those clip appliers that employ clip magazines having a series of teeth or other elements for individually holding and advancing the clips.

The clips 10 of the present invention are formed from discrete wire segments 52 formed about a unique or novel mandrel or anvil 54. Initially, a coil of round wire is fed through a pair of opposed flattening rollers to provide a wire having a flat top and bottom surface. These flat surfaces 22 and 24 eventually become the flat inside and outside surfaces of the surgical clip. The coil of flattened wire is then fed into a machine which forms the longitudinal channel or groove 26 by a stamping process. Subsequently, the wire is cut into discrete segments 52 and the discrete segments 52 are then formed and pressed around a mandrel or anvil 54 to form the lateral notches 34 on the inside surface 24 of the legs as well as the coined or chamfered front surfaces 50 of the legs. Once the final clip is formed it is subjected to tumbling to remove burrs, annealing to soften the metal and polishing to provide a aesthetically pleasing final product.

As seen in FIG. 10, a front former 56 drives the wire segment 52 against the front or lead portion of the mandrel 54. The front portion of the mandrel 54 and the driver 56 are cooperatively shaped to form the crown or curved portion 14 of the clip. Subsequently, a pair of side drivers 58 engage and press the ends of the wire segment 52 into the mandrel 54 to form the legs 12 of the surgical clip 10. As can be seen, the exterior surface 60 of the mandrel is formed with a series of symmetrically spaced vertical protrusions or knives 62 which act to form the lateral channels 34 along the inside surface 24 of the clip legs 12. The mandrel 54 is also provided with a pair of beveled or outwardly flaired vertical surfaces 64. These surfaces 64 form the coined edges 50 at the tips of the respective clip legs. As seen best in FIG. 10, the knife at the tip of the mandrel is V shaped and forms the bending notch 66 at the inside center of the clip. The remaining knives 62 along each side of the mandrel 60 are equally and symmetrically spaced with respect to the corresponding knives 62 on the opposite side. As a result, when a clip is subjected;bjected to the deforming forces of a clip applier, the clip will deform with the longitudinal and lateral notches 26 and 34 in aligned, registered relation. Moreover, the symmetrically placed flaired surfaces 64 of the mandrel 54 provide a clip that has a uniform stack length irrespective of whether the discrete wire 52 segment is evenly or symmetrically formed about the mandrel 54.

A stack length, as shown in FIG. 1 at L, is defined as the distance between the chamfered clip leg tips on abutting clips measured between the point at which the beveled surface joins the inside surface of the clip. Under convention manufacturing techniques, when a wire segment is not properly aligned before it is formed about an anvil, the resulting conventional clip 70 will have one leg longer than the other. Moreover, a conventional clip 70 is not formed with coined leg tips but, rather, the front tips 72 of the legs are flat. As can be seen in the top portion of FIG. 12, the unevenly formed clip 70 does not properly engage the clip in front of it. As a result, the stack length L of the clips is not uniform and the row of clips will soon become unaligned when a force is applied to the last clip to advance the row of clips. Once the clips become unaligned they could easily jam the instrument. The design of the present clip and the apparatus for manufacturing that clip, by providing the symmetrically placed chamfered or coined front edges 50 on the opposed clip legs 12 overcomes this problem and provides a clip of uniform stack length L.

In comparison, as seen in the lower portion of FIG. 12, a wire segment formed about the mandrel 54 of the present invention can similarly be formed off-center and result in a clip having one leg longer than the other. However, under the present invention both of the leg tips 16 will be coined 50 even though one leg is shorter than the other. The critical difference is evident when the clips are placed in a row of forward facing, abuttingly engaged clips. In the case of the clip of the present invention, due to the 45° angle of the chamfer 50 at the front edge of each clip in combination with the 45° angle of the crown of the clip 14, the clip with uneven leg lengths can still uniformly and symmetrically engage the clip in front of it. Consequently, when an advancing force is applied to the last clip in the row, the row of clips will advance without coming out of alignment. Indeed the clips formed by the apparatus of the present invention are self aligning.

Whereas a preferred embodiment and certain alternative designs have been shown described herein, it will be apparent that other modifications, alterations and variations may be made by and it will occur to those skilled in the art to which invention pertains, particularly upon considering the foregoing teachings. For example, the shape of the respective lateral and longitudinal notches 26 and 34, respectively, may be modified by modifying the knives on the mandrel and still function to maintain the clip 10 closed and secured about a blood vessel. Particularly, as shown in FIG. 3B, the lateral channels 34 could be shaped with an inclined front 76 surface rather than a vertical front surface 36 (FIG. 3A) and still promote closure of the clip 10 when lateral forces are applied to the clip. In addition, the mandrel 54 may be formed of a much greater height than the width of the wire segment 52 so that as the knives or cutting edges 62 of the mandrel become dull its height may be adjusted to provide sharpened edges without having to replace the mandrel. It is, therefore, contemplated by the appended claims to cover any such modifications and other embodiments as incorporated those features which constitute the essential features of this invention within the true spirit and scope of the following claims.

What is claimed is:

1. A surgical clip for use with a mechanical clip applying device for occluding the flow of blood through a vein, artery or similar vessel, the clip having first and second opposed legs interconnected at a back end to form a bight portion and spaced at the opposite distal ends, the improvement comprising: longitudinal channel means on the inside surface of each of said opposed legs and extending substantially from the spaced distal end to the bight portion for preventing longitudinal slippage of said clip relative to the vessel after said clip has been deformed about the vessel, said longitudinal channel means defined by an open sided channel having a pair of spaced generally parallel side walls and a bottom surface, a plurality of lateral channel means extending across the inside surface of said first and second opposed legs and traversing said longitudinal channel means for preventing lateral slippage of said clip relative to the vessel after said clip has been deformed about the vessel, said lateral channel means being defined by a bottom wall generally parallel to the inside surface of said leg in which it is formed, and bight and distal walls extending between said bottom wall and said inside surface, said distal wall being generally planar and forming an acute angle with said bottom wall.

2. The surgical clip of claim 1 wherein upon deformation of said clip about a vessel said first and second opposed legs are placed in overlying registered relation, and wherein said longitudinal channel means of the first leg is placed in overlying registered relation with the longitudinal channel means of the second leg and said spaced generally parallel side walls of said longitudinal channel means of the first leg co-act with the spaced generally parallel side walls of the overlying registered longitudinal channel means of the second leg to form a generally rectilinear longitudinal vessel restricting chamber with spaced, substantially vertical side walls to prevent longitudinal slippage of the clip relative to the vessel, and said lateral channel means in the first leg are placed in overlying aligned relation with said lateral channel means in the second leg and said distal wall of said lateral channel means of the first leg co-acts with the distal wall of said overlying lateral channel means of the second leg to form multiple lateral vessel restricting chambers having distal walls to prevent lateral slippage of said clip relative to the vessel.

3. The surgical clip of claim 1 wherein each of the first and second legs has a bevelled inside distal end to provide a generally planar surface, each of said bevelled ends having an edge connecting said bevelled ends to the inside surface of the associated leg whereby said bevelled ends abuttingly co-act to encapture the vessel and to prevent scissoring of said legs upon closure of the clip.

4. The surgical clip of claim 3 wherein said bevelled ends are disposed at a 45 degree angle to the inside surface of the legs.

5. A surgical clip for occluding the flow of a body fluid through a vein, artery or similar vessel for use with a mechanical clip applying device adapted to hold a plurality of the clips abuttingly arranged in a forward facing row and deform each successive clip to provide two generally parallel legs joined at a bight portion, the clip, prior to deformation, having proximal leg portions connected together at the bight portion and forming an angle therebetween, and distal leg portions, each distal leg portion being connected to its respective proximal leg portion at an obtuse angle, the distal and proximal leg portions being substantially coplanar and the distal leg portions being substantially parallel, the improvement comprising bevelled formations at the free ends of the distal leg portions disposed and arranged to cause each clip to have a clip stack length equal to the clip stack length of every other clip in the row of clips and to engage the proximal leg portions of the preceding clip in the row of clips to cause the row of clips to advance while maintaining linear alignment upon the application of a force to the last clip in the row of clips.

6. The surgical clip of claim 5 wherein each of said bevels is at about 45 degrees to the longitudinal axis of the respective distal leg portion.

7. The surgical clip of claim 5 wherein there is a notch at said bight on the inner surface of the legs whereby the formation of the bight ends of said proximal leg portions is facilitated.

* * * * *

UNITED STATES PATENT AND TRADEMARK OFFICE
CERTIFICATE OF CORRECTION

PATENT NO. : 4,844,066

DATED : July 4, 1989

INVENTOR(S) : Stein

It is certified that error appears in the above-identified patent and that said Letters Patent is hereby corrected as shown below:

Title page, in the "References Cited" Section, under other prior art insert the following --One sheet of drawings showing commercial clips--.

Signed and Sealed this

Twenty-ninth Day of May, 1990

*Attest:*

HARRY F. MANBECK, JR.

*Attesting Officer*　　*Commissioner of Patents and Trademarks*